United States Patent [19]

Gregory

[11] 4,084,951

[45] Apr. 18, 1978

[54] SILICON COMPOUNDS CONTAINING NUCLEOFUGAL PHOSPHATE GROUP AND METHOD OF REGULATING PLANT GROWTH THEREWITH

[75] Inventor: Maurice James Gregory, Kuala Lumpur, Malaysia

[73] Assignee: Ciba-Geigy AG, Switzerland

[21] Appl. No.: 576,291

[22] Filed: May 12, 1975

Related U.S. Application Data

[62] Division of Ser. No. 249,553, May 2, 1972, Pat. No. 3,898,257.

[30] Foreign Application Priority Data

May 3, 1971 United Kingdom .............. 12798/71

[51] Int. Cl.$^2$ .......................... A01N 9/36; C07F 7/02; C07F 7/04
[52] U.S. Cl. ................................. 71/86; 71/87; 260/448.2 N; 260/448.8 R
[58] Field of Search ............. 71/86, 87; 260/448.8 R, 260/448.2 N

[56] References Cited

U.S. PATENT DOCUMENTS

| | | | |
|---|---|---|---|
| 2,963,503 | 12/1960 | Marsden .................. | 260/448.8 R |
| 3,122,581 | 2/1964 | Pike ....................... | 260/448.8 R |
| 3,275,501 | 9/1966 | Schrader et al. ......... | 260/963 X |
| 3,276,977 | 10/1966 | Willmund et al. ........ | 260/963 X |
| 3,546,179 | 12/1970 | Koller .................... | 260/448.8 R |
| 3,641,223 | 2/1972 | Schlor et al. ............ | 260/961 |
| 3,830,886 | 8/1974 | Davis et al. ............ | 260/963 X |
| 3,843,670 | 10/1974 | Moser et al. ............ | 71/87 X |
| 3,912,493 | 10/1975 | Foery et al. ............. | 71/86 X |

Primary Examiner—Joseph Paul Brust
Attorney, Agent, or Firm—Wenderoth, Lind & Ponack

[57] ABSTRACT

Compounds containing the grouping X—CH$_2$—CH$_2$—Si ≡ where X is a nucleofugal phosphate group, are useful as plant regulating agents, particularly as yield stimulants for *Hevea brasiliensis*.

12 Claims, No Drawings

SILICON COMPOUNDS CONTAINING NUCLEOFUGAL PHOSPHATE GROUP AND METHOD OF REGULATING PLANT GROWTH THEREWITH

This application is a divisional of my Ser. No. 249,553, filed on May 2, 1972 now U.S. Pat. No. 3,898,257.

This invention relates to chemical compounds useful as —X, (x) regulators, to plant growth regulating compositions containing them, and to processes or methods of regulating the growth of plants.

The useful effects which can be achieved by applying the compounds of the invention to plants are diverse, as they are with numerous other plant growth regulators, and include the accelerated ripening of fruits, the acceleration of abscission, the breaking of dormancy in buds, shoots, tubers, corms and rhizomes and other plant growth regulation effects. Particularly notable in our experiments is the effect of applying the compounds of the invention to the bark of the rubber tree *Heavea brasiliensis*, which effect is to prolong the flow of latex from the tree on tapping and thereby increase the yield of rubber from the tree.

According to the invention there is provided a plant growth regulator comprising a compound containing the chemical grouping:

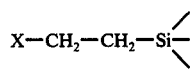
(I)

in which X is a nucleofugal group selected from

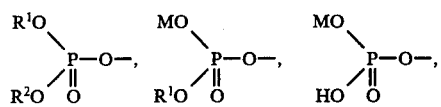

where M is a hydrogen or metal atom or ammonium radical; $R^1$ is a substituted or unsubstituted hydrocarbon group (open chain or cyclic) containing from 1 to 18 carbon atoms; $R^2$ is defined as (but not necessarily identical with) $R^1$.

In heterolytic fragmentation of organic compounds, which is by far the most common type of fragmentation in solution, one group (the nucleofugal group) leaves with the electron pair by which it was originally attached to the rest of the molecule, i.e. as a nucleofuge. This group thereby becomes more negative by one charge unit and is converted into a nucleofugal fragment. This is usually an anion, e.g. halide, sulphonate, phosphate or thiocyanate, but may be a neutral group, e.g. one derived from a pyridinium or ammonium group.

While we do not wish to be bound by any theory of how our invention works, we believe that the silicon compounds with which the invention is concerned act by decomposing in the presence of water in the plant tissues to provide ethylene, and that it is this ethylene which is mainly responsible for exerting the growth regulating effect. We further believe that any compound containing the grouping of formula I above is capable of decomposing in the presence of water to provide ethylene.

It will be appreciated that the rate of decomposition of these silicon compounds is important as far as their growth regulating properties are concerned. In many cases it is believed that the most effective growth regulation is achieved by a controlled slow release of ethylene in the plant tissues, sometimes over a period of a month or more. The rate of decomposition in water of the silicon compounds with which this invention is concerned can be varied over a wide range by an appropriate selection of the group X and of the three groups (other than —CH$_2$CH$_2$X) attached to the silicon atom. This phenomenon is readily seen by reference to the following data.

Half lives of various silanes in 0.1M aqueous phosphate buffers at pH 7 and 25°.

| Compound | Half-life |
| --- | --- |
| 2-chloroethyltrimethoxysilane | 20 mins. |
| 2-chloroethyltriisopropoxysilane | 3 weeks |
| 2-chloroethyltri-n-dodecanoxysilane | 2½ hours |
| 2-chloroethyltrimethylsilane | <1 min. |
| ethyl methyl 2-(trimethoxysilyl)-ethyl sulphonium iodide | 14 hours |

It will also be understood that while the rate of decomposition of the silanes in aqueous solution might be expected to influence the rate at which ethylene is generated in the plant tissue, other influences also control this rate. Of equal or greater importance is the diffusion of the silanes from the formulation medium into the aqueous portions of the plant. Thus it would be expected that a solution of an oil soluble/water insoluble silane applied to a plant might under suitable conditions liberate ethylene more slowly than a less reactive water soluble silane applied similarly. This phenomenon is readily seen by reference to the following experiment.

Three *Hevea brasiliensis* seedlings were treated with 2-chloroethyltrimethoxysilane (2 μl) applied as a neat liquid. Three similar seedlings were treated with the same weight of compound applied as a 12% solution in petroleum jelly. The following average yields of rubber were obtained (yield in mg of dry rubber, expressed as a percentage of pretreatment yields in parentheses).

| Time after treatment in days: | 3 | 7 | 12 | 16 | 24 | 30 | 34 | 42 |
| --- | --- | --- | --- | --- | --- | --- | --- | --- |
| Plants treated with neat compounds: | 2.1 (230) | 2.2 (245) | 1.3 (145) | 1.1 (122) | 0.9 (100) | 0.8 (90) | 1.2 (134) | 1.0 (112) |
| Plants treated with solution: | 2.2 (160) | 2.3 (164) | 2.3 (164) | 3.0 (215) | 2.2 (160) | 2.3 (164) | 1.8 (128) | 0.9 (65) |

The more prolonged response to the silane in petroleum jelly can be seen from the above data.

The silicon compounds with which the invention is concerned may be regarded as having the formula:

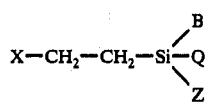
(II)

where X has been defined above. B, Q and Z may be all the same or different, and may be selected from the following groups by way of example:

(i) halogen, e.g. chlorine or bromine,
(ii) alkyl having from 1 to 18 carbon atoms, e.g. methyl, ethyl, isopropyl, tert.-butyl, dodecyl,
(iii) alkoxy having from 1 to 18 carbon atoms, e.g. methoxy, ethoxy, isopropoxy, tert.-butoxy, dodecanoxy,
(iv) aryl, e.g. phenyl, tolyl,
(v) hydroxyl,
(vi) thio or alkylthio,
(vii) dialkylamino

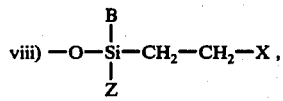

(ix) —CH$_2$—CH$_2$-X, (x) substituted alkyl or alkoxy, e.g. acyloxy-, hydroxy- or halogen-substituted alkyl or alkoxy.

This list is not exhaustive, but includes those groups which are likely to be of interest from a commercial standpoint. As stated above, there is no pratical restriction on the nature of the groups B, Q and Z.

All these silicon compounds are hydrolysed by water with the production of ethylene. In many cases, however, the first thing that happens when the compounds are mixed with water is the replacement of the groups B, Q or Z with hydroxyl groups. This appears in general to be the case when B, Q and Z are alkoxy, halogen, thio, alkylthio, dialkylamino or acyloxy groups, but not when B, Q and Z are alkyl or siloxane groups. So, in many cases, the compound which is hydrolysed with the production of ethylene in a 2-substituted-ethyl hydroxy silane.

It is surmised that the speed of decomposition of the compounds of formula II may vary as follows when X is changed, the groups B, Q and Z remaining constant:

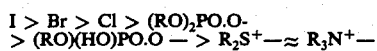

It is further surmised that the speed of decomposition of the compounds of formula II may vary as follows when, say, B is changed, the groups X and, say, Q and Z remaining constant:

alkyl≈aryl > RS— ≈ R$_2$N ≈ HO— ≈ RO—

>> ≡

These sequences can only provide, at best, a rough guide to the rate of decomposition of any particular compound.

These silicon compounds vary in physical properties from volatile liquids to crystalline solids. Although the marjority of compounds are oil soluble and substantially insoluble in water, water soluble derivatives can be obtained when the group X is ionic in nature, or when B, Q or Z contain hydrophilic groups. While water solutions or suspensions are not normally suitable for the storage or transport of the silicon compounds, due to their susceptibility to decomposition, it may be convenient to make up aqueous compositions for immediate application. Such aqueous compositions should preferably have a pH of not more than 5 in order to minimise the initial unwanted hydrolysis before the compound reaches the plants.

These compounds may be made by standard methods. In general, the introduction of the desired nucleofulgal group X is effected quite separately from the introduction of the desired groups B, Q and Z. Thus, for example, 2-chloroethyl trichlorosilane may be reacted with up to 3 moles of an alkanol so as to introduce up to 3 alkoxy groups attached to the silicon atom. The resulting compound may then be reacted with further reagents to introduce the desired group X in place of the 2-chlorine atom.

The invention also includes a composition for regulating plant growth, which composition comprises at least one compound containing the group of formula I where X is a nucleofugal group, in a liquid solvent or dispersion medium, a viscous oil or greasy medium, or a pulverulent and/or granular solid carrier. Such compositions may contain, if desired, a surface active agent.

The composition based on solid carriers may be applied in the form of powder or granules. Suitable solid carriers include, for example, kaolin, talc, bentonite, calcium carbonate, gypsum, magnesia, vermiculite, Fuller's earth and kieselguhr.

Compositions based on liquid carriers may contain water and/or organic liquids as the carrier medium, and the active ingredient may be in the form of a solution, dispersion or emulsion in the liquid carrier.

Surface active agents, 8.65 used, may be of the anionic, cationic or non-ionic type. Suitable agents of the anionic type include, for example, fatty acid salts, salts of aliphatic monoesters of sulphuric acid, e.g. sodium dodecyl sulphate, salts of sulphonated aromatic compounds, e.g. sodium dodecylbenzene sulphonate, salts of lignosulphonic acid and salts of alkyl-naphthalene sulphonic acids, e.g. sodium butylnaphthalene sulphonate. Suitable agents of the cationic type include, for example, quaternary ammonium compounds, e.g. cetyltrimethylammonium bromide, dodecyltrimethylammonium chloride. Suitable agents of the non-ionic type include, for example, the condensation products of ethylene oxide with fatty alcohols such as oleyl alcohol, cetyl alcohol and lauryl alcohol, or with alkylphenols such as nonylphenol and octyl cresol. Also included are the partial esters derived from long chain fatty acids and hexitol anhydrides (e.g. sorbitol monolaurate) and the condensation products of such partial esters with ethylene oxide. However, it is not advisable to use non-ionic surfactants containing free hydroxyl groups when the silicon compounds contain groups (B, Q and Z) attached to the silicon atom, such as halogen atoms, which are liable to react chemically with hydroxyl groups.

Compositions which are to be used in the form of solutions, dispersions or emulsions of the active ingredient in a liquid carrier are generally supplied in the form of concentrates containing a high proportion of the active ingredient, the concentrate being diluted with water or an organic liquid before use. It is generally convenient for such concentrates to contain between 10% and 80% by weight of the active ingredient. The concentration of active ingredient in compositions actually applied to the plants (or to the locus of the plants) may vary widely according to the purpose for which they are to be used, but will generally contain between 0.001% and 50% by weight of active ingredient.

The rate of application of the silicon compounds will depend on numerous factors, e.g. the plant species to be treated and the particular compound used, and the optimum rate of application may therefore vary widely according to circumstances. As a general guide, however, a rate of application of 0.1 pounds per acre to 20 pounds per acre of the active ingredient is usually suitable when applied to standing vegetation.

As stated above, the compositions of this invention are particularly advantageous for the treatment of *Hevea brasiliensis* to stimulate the yield and prolong the flow of rubber latex therefrom. A convenient technique is to apply the composition to scraped bark just below the tapping cut.

When treating fully grown trees, it is prefered to apply from 50 mg to 1000mg, e.g. from 100 mg to 500 mg, of the silicon compound per tree. The concentration of the compound in the carrier is not critical. It is generally convenient, from a practical viewpoint, to apply a few grams of composition to each tree.

It will generally be found suitable to repeat application of the compounds at from two to six month intervals.

Advantage may be taken of the yield stimulant effect of those compounds, either by tapping the tree at the same intensity, so as to obtain an increased yield of rubber latex, or by reducing the tapping intensity, and hence labour costs, without loss of yield.

A compound which has come into widespread use, as a stimulant of the yield of rubber latex from *Hevea brasiliensis*, is 2-chloroethyl phosphonic acid sold under the Trade Mark Ethrel. The following advantages attach to some compounds according to the present invention in comparison with Ethrel:

A. Results indicate that some compounds according to the present invention have a greater and longer-lasting effect on latex yield than Ethrel;

B. The compounds of this invention are generally safe compared to Ethrel, which is a strong acid and requires careful handling;

C. Lipophilic compounds of this invention are less likely to be washed off the tree, e.g. by rain, than Ethrel, which is rather water-soluble;

D. The range of compounds of this invention have a wide spectrum of water solubility and of rate of hydrolysis, so that different compounds may be selected suitable for different applications.

The following Examples illustrate the invention.

EXAMPLE 1

Preparaion of 2-(trimethylsilyl) ethyl diethyl phosphate.

A solution of 2-(trimethylsilyl)ethanol (1.28 g, 0.01 mole), and pyridine (0.79 g, 0.010 mole) in carbon tetrachloride (10 ml) was allowed to react with diethyl phosphorochloridate (0.0105 mole) at 0° overnight. Pyridine hydrochloride was filtered off and the solvent was removed to yield the product as a viscous oil.

Other phosphate esters may be made using this procedure, starting from other alkyl- or aryl-substituted silyl ethanols.

EXAMPLE 2

Preparation of diphenyl 2-(trimethylsilyl)-ethyl phosphate.

A solution of 2-(trimethylsilyl)ethanol (22 g) diphenylphosphorochloridate (44.5 g) and pyridine (13.2 g) in carbon tetrachloride (200 ml) was left at room temperature for 2½ days. The solution was filtered and passed through an alumina column (200 g), eluting with a further 2 × 200 ml of carbon tetrachloride. Removal of the solvent from the eluate left diphenyl 2-(trimethylsilyl)-ethyl phosphate (35.5 g) as a colourless oil.

(Found: C, 58.1%; H, 6.6%; P, 8.7%. $C_{17}H_{23}PO_3Si$ requires: $C_1$ 58.3%; H, 6.6%; P, 8.9%).

EXAMPLE 3

Preparation of 2-(trimethylsilyl)ethyl dihydrogen phosphate di-cyclohexylammonium salt.

A solution in acetonitrile (30 ml) of crystalline phosphoric acid (2.0 g) and triethylamine (4.0 g) was added dropwise over 4 hours to a mixture of 2-(trimethylsilyl)-ethanol (3.0 g) and and trichloroacetonitrile (8.6 g) at room temperature. The mixture was left overnight, diluted with acetone (200 ml) and cyclohexylamine (15 ml) was added. The precipitate was collected and recrystallised from water and then ethanol 10% cyclohexylamine to give the cyclohexylammonium salt, (1.3 g) m.p. 252°–255°.

($C_{17}H_{41}H_2Sio_4P$ requires: C, 51%; H, 10.4%; N, 7.7%; and a C:N ratio of 7.3. Found: C, 47.6%; H, 10.6%; N. 6.5% C:N ratio 7.3).

EXAMPLE 4

Preparation of di-n-butyl 2-(di-n-butylmethylsily)-ethyl phosphate.

Dibutylphosphorochloridate (3.74 g) was added to a solution of 2-(di-n-butyl methylsilyl)-ethanol (3 g) and pyridine (1.04 g) in carbon tetrachloride (10 ml). The mixture was left overnight, filtered, and the filtrate passed through an alumina column (20 g), eluting with a further 3 × 20 ml of carbon tetrachloride. Removal of the solvent under vacuum left the phosphate as a colourless oil (2.7 g).

(Found: C, 58.6%; H, 11.3%; $C_{19}H_{43}S_iO_4P$ requires: C, 58.0%; H, 11.0%.

EXAMPLE 5

Preparation of diethyl 2-(diphenyl methylsilyl)-ethyl phosphate

The reaction described in Example 10 was carried out using 2-(diphenylmethylsilyl)-ethanol (2.25 g), diethyl-phosphorochloridate (1.35 g), and pyridine (0.6 g) in carbon tetrachloride (10 ml). Diethyl 2-(diphenylmethylsilyl)ethyl phosphate was obtained as a colourless oil (1.35 g) ($C_{17}H_{23}Si\ O_4P$ requires: C, 60.5%; H, 7.1%; Found: C 63.4%; H, 7.8%).

EXAMPLE 6

A solution of 20% w/w of diphenyl 2-(trimethylsilyl-)ethylphosphate in palm oil was applied to 1½ inch wide strip of scraped bark just below the tapping cut of *Hevea brasiliensis* trees (Clone Tjirandji 1). The trees were tapped on alternate days using a half-spiral tapping cut. The yield of dried rubber obtained over a four-week period was measured. The mean yields over two weeks, expressed as grams of dry rubber per tree per tapping was 45.5 (194% of control).

I claim:

1. A compound having the formula:

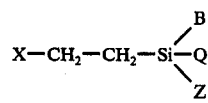

wherein X is selected from

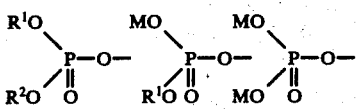

where M is hydrogen or ammonium; R¹ and R² are the same or different and each is an open chain or cyclic hydrocarbon group containing from 1 to 18 carbon atoms;

and B, Q and Z are the same or different and each is selected from the group consisting of:
(i) chlorine or bromine,
(ii) alkyl having from 1 to 18 carbon atoms,
(iii) alkoxy having from 1 to 18 carbon atoms,
(iv) phenyl or tolyl,
(v) hydroxyl,
(vi) thiol or alkylthio,
(vii) dialkylamino,

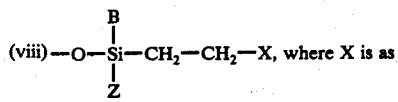

defined above, and B and Z are as defined in any one of groups (i) to (vii), (ix) and (x) hereof,
(ix) —CH₂—CH₂—X, where X is as defined above,
(x) hydroxy-substituted or halogen-substituted alkyl or alkoxy,
said compound being capable of decomposing in water to provide ehtylene.

2. A compound as claimed in claim 1, wherein R¹ and R² are the same or different and each is an open chain or cyclic hydrocarbon group containing from 1 to 8 carbon atoms; B, Q and Z are the same or different and each is selected from the group consisting of alkyl having from 1 to 8 carbon atoms, phenyl and tolyl; and M is hydrogen or ammonium.

3. A compound as claimed in claim 1 which is 2-(trimethylsilyl) ethyl diethyl phosphate; diphenyl 2-(trimethylsilyl)-ethyl phosphate; 2-(trimethylsilyl) ethyl dihydrogen phosphate di-cyclohexylammonium salt; di-n-butyl 2-(di-n- butylmethylsilyl)-ethyl phosphate or diethyl 2-(diphenyl methylsilyl)-ethyl phosphate.

4. A compound as claimed in claim 2 wherein each of R¹, R², B, Q and Z is an alkyl hydrocarbon group containing from 1 to 8 carbon atoms.

5. A composition for regulating plant growth, which composition comprises from 0.001% to 50% of a compound as claimed in claim 1 in a liquid solvent.

6. A composition for regulating plant growth, which composition comprises from 0.001% to 50% of a compound as claimed in claim 1 in a dispersion medium.

7. A composition for regulating plant growth, which composition comprises from 0.001% to 50% of a compound as claimed in claim 1 in a viscous oily medium.

8. A composition for regulating plant growth, which composition comprises from 0.001% to 50% of a compound as claimed in claim 1 in a greasy medium.

9. A composition for regulating plant growth, which composition comprises from 0.001% to 50% of a compound as claimed in claim 1 in admixture with pulverulent solid matter.

10. A composition for regulating plant growth, which composition comprises from 0.001% to 50% of a compound as claimed in claim 1 in admixture with granular solid matter.

11. A method of regulating plant growth, which method comprises applying to a plant a compound as claimed in claim 1 in an amount of from 0.1 pounds to 20 pounds of active ingredient per acre.

12. A method of regulating plant growth, which method comprising applying to a plant a compound as claimed in claim 3 in an amount of from 0.1 pounds to 20 pounds of active ingredient per acre.

* * * * *